(12) United States Patent
Noda et al.

(10) Patent No.: US 12,357,259 B2
(45) Date of Patent: Jul. 15, 2025

(54) RADIATION IMAGING APPARATUS, RADIATION IMAGING METHOD, AND NON-TRANSITORY COMPUTER-READABLE STORAGE MEDIUM

(71) Applicant: CANON KABUSHIKI KAISHA, Tokyo (JP)

(72) Inventors: Takeshi Noda, Kanagawa (JP); Sota Torii, Tokyo (JP); Katsuro Takenaka, Saitama (JP); Akiya Nakayama, Kanagawa (JP); Daisuke Sato, Tochigi (JP); Haruki Iwai, Tochigi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 216 days.

(21) Appl. No.: 18/330,115

(22) Filed: Jun. 6, 2023

(65) Prior Publication Data
US 2023/0309942 A1 Oct. 5, 2023

Related U.S. Application Data

(63) Continuation of application No. PCT/JP2021/047537, filed on Dec. 22, 2021.

(30) Foreign Application Priority Data

Feb. 9, 2021 (JP) ................. 2021-019226

(51) Int. Cl.
*A61B 6/00* (2024.01)
*A61B 6/40* (2024.01)
(Continued)

(52) U.S. Cl.
CPC ............... *A61B 6/52* (2013.01); *A61B 6/405* (2013.01); *A61B 6/4085* (2013.01); *A61B 6/505* (2013.01); *G06T 7/0014* (2013.01); *G06T 2207/10116* (2013.01); *G06T 2207/10144* (2013.01); *G06T 2207/20224* (2013.01); *G06T 2207/30012* (2013.01)

(58) Field of Classification Search
CPC .................................................... A61B 6/505
See application file for complete search history.

(56) References Cited

U.S. PATENT DOCUMENTS 7,342,221 B2   3/2008   Takenaka
7,343,000 B2   3/2008   Kameshima
(Continued)

FOREIGN PATENT DOCUMENTS

JP   2009-101157 A   5/2009
JP   2011-245117 A   12/2011

OTHER PUBLICATIONS

U.S. Appl. No. 18/365,395, Takashi Takasaki, filed Aug. 4, 2023.

*Primary Examiner* — Dani Fox
(74) *Attorney, Agent, or Firm* — VENABLE LLP

(57) ABSTRACT

A radiation imaging apparatus includes: an image obtaining unit configured to obtain image data corresponding to incident radiation; and an image processing unit configured to perform first bone density measurement based on image data obtained by the image obtaining unit with a first exposure field and perform second bone density measurement based on image data obtained by the image obtaining unit with a second exposure field narrower than the first exposure field.

25 Claims, 9 Drawing Sheets

(51) Int. Cl.
*A61B 6/50* (2024.01)
*G06T 7/00* (2017.01)

(56) References Cited

U.S. PATENT DOCUMENTS

| | | | |
|---|---|---|---|
| 7,381,963 B2 | 6/2008 | Endo |
| 7,386,089 B2 | 6/2008 | Endo |
| 7,403,594 B2 | 7/2008 | Endo |
| 7,408,167 B1 | 8/2008 | Kameshima |
| 7,421,063 B2 | 9/2008 | Takenaka |
| 7,442,939 B2 | 10/2008 | Yagi |
| 7,466,345 B2 | 12/2008 | Kameshima |
| 7,476,027 B2 | 1/2009 | Takenaka |
| 7,491,960 B2 | 2/2009 | Takenaka |
| 7,514,663 B2 | 4/2009 | Yagi |
| 7,514,690 B2 | 4/2009 | Endo |
| 7,532,706 B2 | 5/2009 | Kameshima |
| 7,541,591 B2 | 6/2009 | Endo |
| 7,550,733 B2 | 6/2009 | Endo |
| 7,573,038 B2 | 8/2009 | Yokoyama |
| 7,573,041 B2 | 8/2009 | Kameshima |
| 7,613,277 B2 | 11/2009 | Takenaka |
| 7,629,587 B2 | 12/2009 | Yagi |
| 7,645,995 B2 | 1/2010 | Yagi |
| 7,683,337 B2 | 3/2010 | Takenaka |
| 7,696,484 B2 | 4/2010 | Yokoyama |
| 7,718,973 B2 | 5/2010 | Endo |
| 7,724,874 B2 | 5/2010 | Kameshima |
| 7,732,776 B2 | 6/2010 | Takenaka |
| 7,732,778 B2 | 6/2010 | Yokoyama |
| 7,750,309 B2 | 7/2010 | Endo |
| 7,791,034 B2 | 9/2010 | Kameshima |
| 7,791,035 B2 | 9/2010 | Yokoyama |
| 7,847,263 B2 | 12/2010 | Yagi |
| 7,850,367 B2 | 12/2010 | Takenaka |
| 7,869,568 B2 | 1/2011 | Yokoyama |
| 7,880,145 B2 | 2/2011 | Yagi |
| 7,989,772 B2 | 8/2011 | Yagi |
| 8,107,588 B2 | 1/2012 | Kameshima |
| 8,167,486 B2 | 5/2012 | Takenaka |
| 8,222,611 B2 | 7/2012 | Yagi |
| 8,247,779 B2 | 8/2012 | Kameshima |
| 8,355,594 B2 | 1/2013 | Noda |
| 8,576,294 B2 | 11/2013 | Kameshima |
| 8,655,034 B2 | 2/2014 | Noda |
| 8,723,996 B2 | 5/2014 | Yokoyama |
| 8,744,210 B2 | 6/2014 | Noda |
| 8,792,024 B2 | 7/2014 | Takenaka |
| 8,809,795 B2 | 8/2014 | Takenaka |
| 8,829,438 B2 | 9/2014 | Sato |
| 8,923,589 B2 | 12/2014 | Noda |
| 9,014,450 B2 | 4/2015 | Noda |
| 9,048,154 B2 | 6/2015 | Takenaka |
| 9,052,400 B2 | 6/2015 | Saruta |
| 9,128,196 B2 | 9/2015 | Sato |
| 9,134,432 B2 | 9/2015 | Iwashita |
| 9,234,966 B2 | 1/2016 | Sugawara |
| 9,423,512 B2 | 8/2016 | Sato |
| 9,445,030 B2 | 9/2016 | Yagi |
| 9,462,989 B2 | 10/2016 | Takenaka |
| 9,468,414 B2 | 10/2016 | Ryu |
| 9,470,800 B2 | 10/2016 | Iwashita |
| 9,470,802 B2 | 10/2016 | Okada |
| 9,541,653 B2 | 1/2017 | Iwashita |
| 9,655,586 B2 | 5/2017 | Yagi |
| 9,737,271 B2 | 8/2017 | Iwashita |
| 9,812,474 B2 | 11/2017 | Yagi |
| 9,820,713 B2 | 11/2017 | Noda |
| 9,953,414 B2 | 4/2018 | Noda |
| 9,971,046 B2 | 5/2018 | Ryu |
| 9,980,685 B2 | 5/2018 | Iwashita |
| 9,989,656 B2 | 6/2018 | Sato |
| 10,009,990 B2 | 6/2018 | Takenaka |
| 10,197,684 B2 | 2/2019 | Terui |
| 10,349,914 B2 | 7/2019 | Takenaka |
| 10,416,323 B2 | 9/2019 | Ryu |
| 10,441,238 B2 | 10/2019 | Terui |
| 10,716,522 B2 | 7/2020 | Sato |
| 10,741,296 B2 | 8/2020 | Sasaki |
| 11,047,808 B2 | 6/2021 | Iwashita |
| 11,047,994 B2 | 6/2021 | Terui |
| 11,153,511 B2 | 10/2021 | Tezuka |
| 11,166,693 B2 | 11/2021 | Saigusa |
| 11,185,301 B2 | 11/2021 | Torii |
| 11,187,816 B2 | 11/2021 | Takenaka |
| 11,280,919 B2 | 3/2022 | Takenaka |
| 11,303,831 B2 | 4/2022 | Iwashita |
| 11,357,455 B2 | 6/2022 | Noda |
| 11,360,034 B2 | 6/2022 | Torii |
| 11,375,098 B2 | 6/2022 | Saigusa |
| 11,430,161 B2 | 8/2022 | Iwashita |
| 11,531,122 B2 | 12/2022 | Terui |
| RE49,401 E | 1/2023 | Iwashita |
| 11,635,392 B2 | 4/2023 | Noda |
| 11,686,691 B2 | 6/2023 | Iwashita |
| 2009/0103679 A1* | 4/2009 | Jabri ............... A61B 6/06 378/70 |
| 2010/0135458 A1* | 6/2010 | Agrawal ............. A61B 6/482 378/208 |
| 2021/0118193 A1 | 4/2021 | Torii |
| 2021/0236078 A1 | 8/2021 | Noda |
| 2022/0047238 A1 | 2/2022 | Terui |
| 2022/0142597 A1 | 5/2022 | Noda |
| 2022/0167935 A1 | 6/2022 | Iwashita |
| 2022/0294973 A1 | 9/2022 | Salgusa |
| 2022/0401054 A1 | 12/2022 | Taya |
| 2023/0258834 A1 | 8/2023 | Ina |

\* cited by examiner

RADIATION IMAGING APPARATUS, RADIATION IMAGING METHOD, AND NON-TRANSITORY COMPUTER-READABLE STORAGE MEDIUM

CROSS-REFERENCE TO RELATED APPLICATIONS

This application is a Continuation of International Patent Application No. PCT/JP2021/047537, filed Dec. 22, 2021, which claims the benefit of Japanese Patent Application No. 2021-019226, filed Feb. 9, 2021, both of which are hereby incorporated by reference herein in their entirety.

BACKGROUND OF THE INVENTION

Field of the Invention

The present invention relates to a radiation imaging apparatus, a radiation imaging method, and a non-transitory computer-readable storage medium and, more particularly, to a radiation imaging technique applicable to the measurement of a bone density.

Background Art

People affected with osteoporosis have increased in number with aging. As a technique for osteoporosis diagnosis, there is known bone density measurement based on dual energy X-ray absorptiometry (to be referred to as DXA hereinafter) using X-rays with two different energies.

A general DXA apparatus is generally designed to perform measurement by switching and scanning X-ray fan beams having different energies at high speed. Recently, there have been developed a technique of performing bone density measurement with DXA by performing a cone-beam imaging operation using a flat panel detector (to be referred to as an FPD hereinafter) formed by stacking two X-ray detection layers and a technique that can perform bone density measurement with DXA by performing an imaging operation twice with X-rays having different energies using a single-layer FPD.

Patent literature 1 discloses a technique of measuring a bone density by correcting the scattered rays of an X-ray image in a wide range using an X-ray image in a narrow range.

CITATION LIST

Patent Literature

PTL 1: Japanese Patent Laid-Open No. 2011-245117

Bone density measurement is often performed by measuring both the lumbar vertebra that tends to suffer a temporal change and the femur proximal portion in which serious damage tends to be left upon bone fracture. Although using a flat panel detector and X-ray cone beams can simultaneously image the lumbar vertebra and femur proximal portion in a short time, using a wide exposure field can reduce the measurement accuracy due to scattered rays.

The technique disclosed in patent literature 1 has a problem that the examination efficiency can decrease and the dosage on an object can increase because of the need to perform imaging four times upon changing the exposure range and the X-ray exposure conditions.

SUMMARY OF THE INVENTION

The present invention provides a radiation imaging technique that can improve the examination efficiency and the measurement accuracy while reducing the dosage on an object.

According to one aspect of the present invention, there is provided a radiation imaging apparatus including: an image obtaining unit configured to obtain image data corresponding to incident radiation; and an image processing unit configured to perform first bone density measurement based on image data obtained by the image obtaining unit with a first exposure field and perform second bone density measurement based on image data obtained by the image obtaining unit with a second exposure field narrower than the first exposure field.

Further features of the present invention will become apparent from the following description of exemplary embodiments with reference to the attached drawings.

DESCRIPTION OF THE EMBODIMENTS

Figure 1:
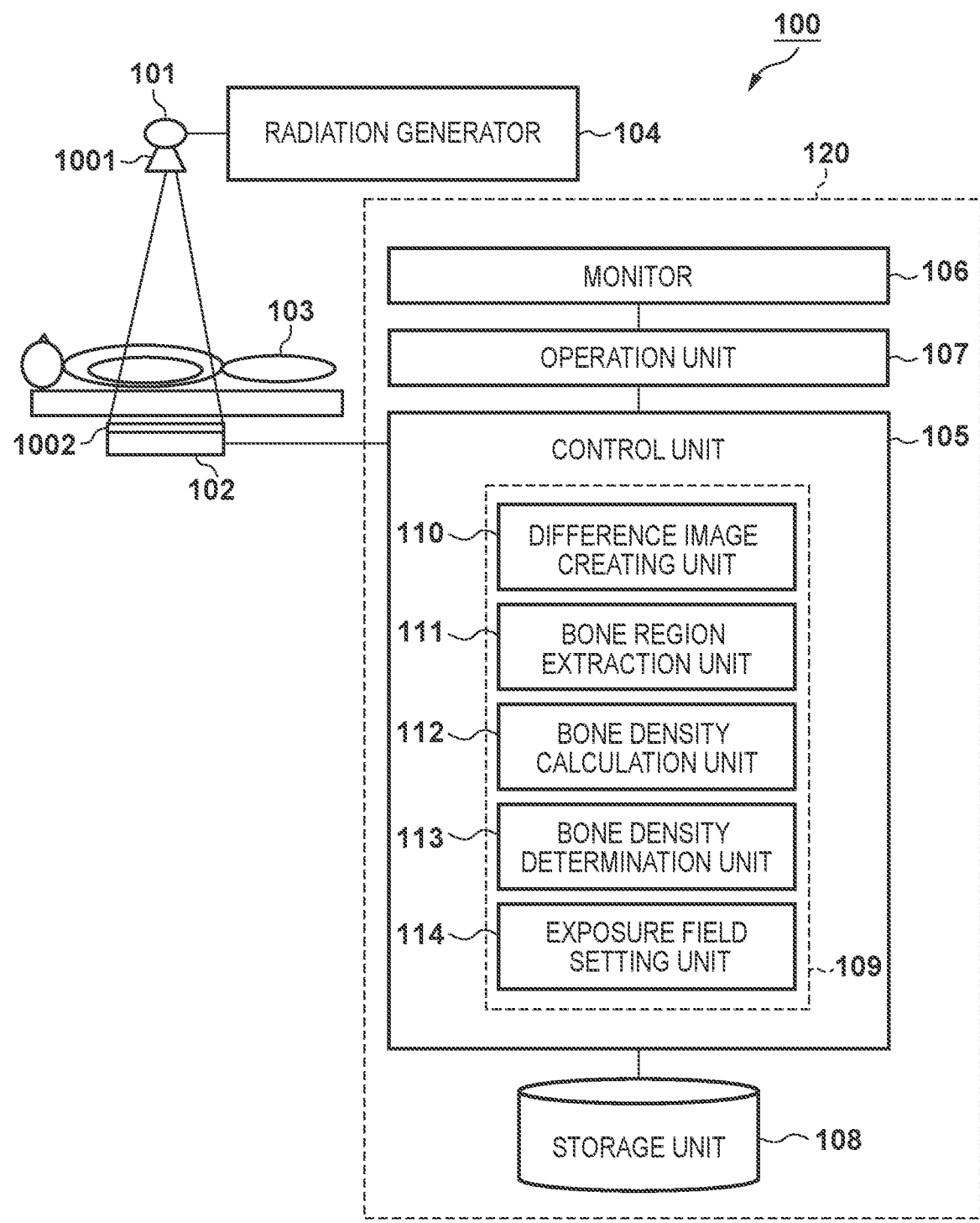
FIG. 1 is a view showing an example of the arrangement of a radiation imaging system according to the first embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

First Embodiment

FIG. 1 is a view showing an example of the arrangement of a radiation imaging system 100 according to the first embodiment of the present invention. The radiation imaging system 100 includes a radiation generator 104, a radiation source 101, a radiation exposure field aperture 1001, a radiation grid 1002, an FPD 102 (radiation flat panel detector), and an information processing apparatus 120. Note that the arrangement of the radiation imaging system 100 is also simply called a radiation imaging apparatus. The information processing apparatus 120 processes information based on the radiation image obtained by imaging an object.

The radiation generator 104 (generating unit) causes the radiation source 101 to generate radiation by supplying a high-voltage pulse to the radiation source 101 upon pressing of the exposure switch. The radiation source 101 irradiates an object 103 with radiation. At this time, the radiation exposure field aperture 1001 prevents radiation from irradiating regions other than a region of interest of the object 103 by narrowing down the irradiation range of radiation. This makes it possible to reduce unnecessary exposure and also reduce scattered rays generated from the object 103. As the radiation grid 1002, a cross grid is preferably used. The cross grid is a grid having slits formed in a lattice pattern in both longitudinal and latitudinal directions. This grid can reduce scattered rays more effectively and uniformly than general grids. This makes it possible to perform imaging with a cone beam and hence makes it unnecessary to perform long-time imaging like imaging with a fan beam or slit scanning. Although the type of radiation to be used is not specifically limited, X-rays are generally used.

When the object 103 is irradiated with radiation from the radiation source 101, the FPD 102 functions as an image obtaining unit and obtains image data in accordance with incident radiation. The FPD 102 obtains a radiation image by accumulating electric charge based on an image signal. The FPD 102 transfers the radiation image to the information processing apparatus 120.

The FPD 102 includes a radiation detection unit (not shown) including a pixel array for creating a signal corresponding to radiation. The radiation detection unit detects radiation transmitted through the object 103 and detects an image signal corresponding to the detected radiation. In the radiation detection unit, each of pixels arranged in an array pattern (two-dimensional region) is provided with, for example, a phosphor (scintillator) that converts incident radiation into light and a photoelectric conversion element that outputs a signal corresponding to the converted light. The photoelectric conversion element of each pixel converts the radiation converted into visible light by the phosphor into an electrical signal and outputs it as an image signal (radiation image).

A control unit 105 includes an image processing unit 109 that processes the radiation image obtained from the FPD 102 and a storage unit 108 that stores the result of image processing and various types of programs. The storage unit 108 can store the radiation image output from the control unit 105, the image processed by the image processing unit 109, and a bone density calculation result.

The image processing unit 109 includes, as functional configurations, a difference image creating unit 110, a bone region extraction unit 111, a bone density calculation unit 112, a bone density determination unit 113, and an exposure field setting unit 114. The functions of these functional configurations each are implemented by using, for example, one or a plurality of CPUs (Central Processing Units) and the program read out from the storage unit 108. The configuration of each unit of the image processing unit 109 may be implemented by an integrated circuit or the like as long as a similar function is implemented. In addition, the internal configuration of the information processing apparatus 120 may include a graphic control unit such as a GPU (Graphics Processing Unit), a communication unit such as a network card, a keyboard, and an input/output control unit such as a display or touch panel.

A monitor 106 displays the radiation image (digital image) obtained by the control unit 105 from the FPD 102 or the image processed by the image processing unit 109. The control unit 105 can control display on the monitor 106. An operation unit 107 can input instructions to the image processing unit 109 and the FPD 102 and accepts the input of instructions via a user interface (not shown).

The control unit 105 obtains an image (bone image) indicating the distribution of bone portions of an object by processing a plurality of radiation images with different energies of radiation irradiating the object by using an energy subtraction method. DXA requires at least two radiation images obtained by imaging with different radiation energies to create one subtraction image. In order to obtain different radiation energies, different voltage pulses may be supplied to the radiation source 101. The object 103 may be irradiated with radiation having different energies from the radiation source 101.

As the FPD 102, an FPD on which radiation detection units (not shown) are stacked may be used. The multilayer FPD 102 detects low-energy radiation by passage through the radiation detection unit on the upper layer and detects high-energy radiation at the radiation detection unit on the lower layer after the quality of the radiation having passed through the radiation detection unit on the upper layer is hardened. This makes it possible to obtain a low-energy radiation image at the radiation detection unit on the upper layer and a high-energy radiation image at the radiation detection unit on the lower layer. Imaging by the multilayer FPD 102 can be done by one-time irradiation with radiation and hence is advantageous in not being influenced by the body motion of the object 103. Note that even a single-layer FPD 102 can obtain an image (low-energy radiation image) with low-energy radiation and an image (high-energy radiation image) with high-energy radiation by one-time irradiation with radiation by performing sampling a plurality of times during one-time irradiation with radiation. Imaging by the FPD 102 may be still-image imaging or moving-image imaging.

Figure 2:
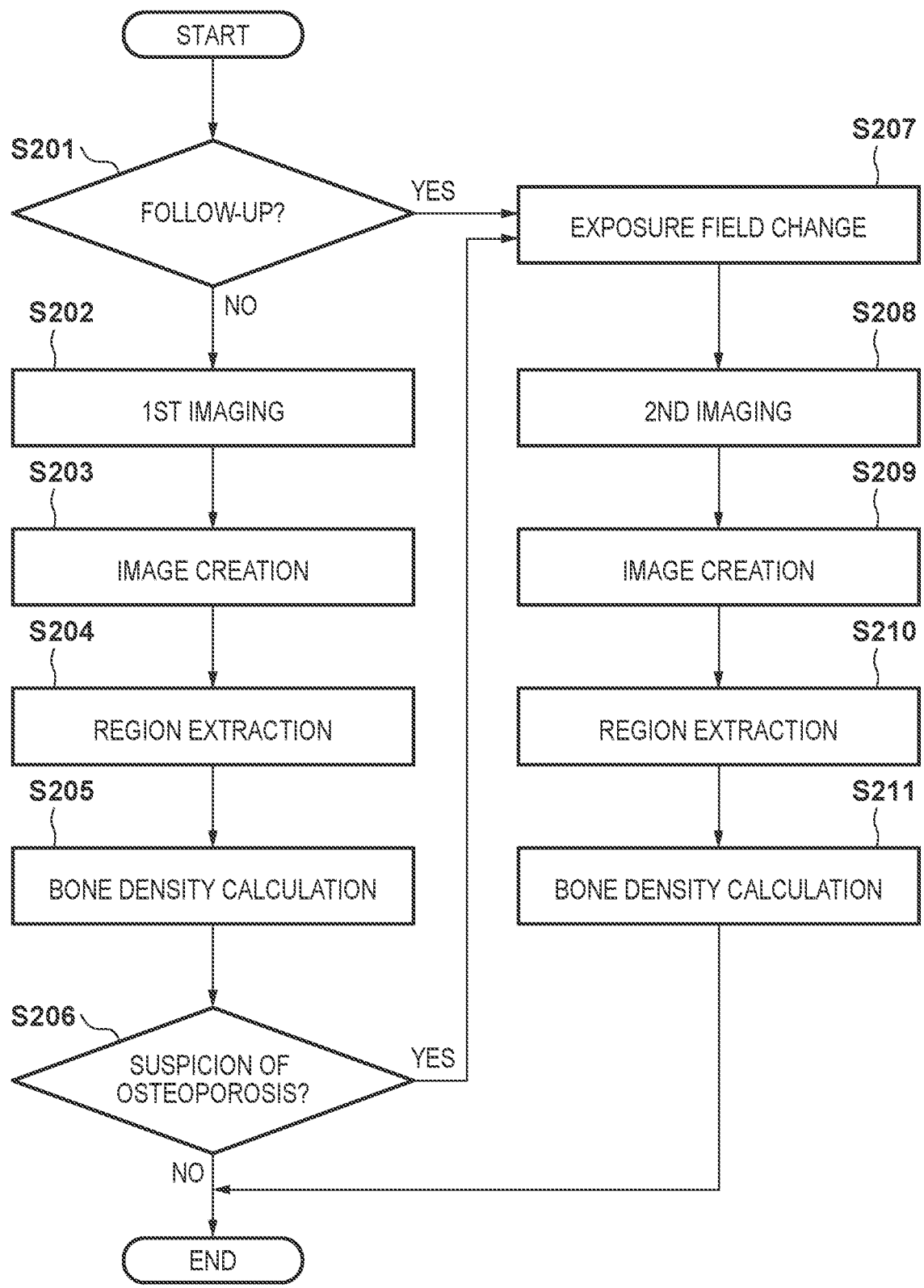
FIG. 2 is a flowchart for explaining a processing procedure in an image processing unit according to the first embodiment.

Processing in the image processing unit 109 according to the first embodiment will be described in detail with reference to the flowchart shown in FIG. 2. Each processing unit (the difference image creating unit 110, the bone region extraction unit 111, the bone density calculation unit 112, and the exposure field setting unit 114) that executes the processing in steps S202 to S205 among the respective steps shown in FIG. 2 functions as a first bone density measuring unit that performs measurement (first bone density measurement) of a bone density based on the image data obtained by the FPD 102 (image obtaining unit) with the first exposure field. Each processing unit (the control unit 105, the difference image creating unit 110, the bone region extraction unit 111, and the bone density calculation unit 112) that executes the processing in steps S208 to S211 functions as a second bone density measuring unit that performs measurement (second bone density measurement) of a bone density based on the image data obtained by the FPD 102 (image obtaining unit) with the second exposure field narrower than the first exposure field. The second bone density measuring unit can measure a bone density with the second exposure field based on the measurement value of the bone density obtained by the first bone density measuring unit and a predetermined threshold.

(S201: Checking of Follow-Up)

In step S201, the control unit 105 uses the information of an object input by the operation unit 107 to determine whether the measurement on the same object is the first measurement or the second or subsequent measurement, that is, a follow-up. The control unit 105 may make this determination in synchronism with a hospital information system HIS and a radiology information system RIS or may make the determination by using information stored in the storage unit 108.

When the process has shifted to the bone density measurement (S208 to S211) by the second bone density measuring unit in the past measurement on the same object, the control unit 105 performs control to start bone density measurement on the same object from bone density measurement by the second bone density measuring unit. When the second bone density measuring unit has performed bone density measurement (S208 to S211), it may have been determined that there is a suspicion of osteoporosis in the object. Accordingly, the control unit 205 determines that the current examination is for follow-up or determination of the effect of medication and proceeds with the process to step S207 to perform the second bone density measurement. In this case, the control unit 105 performs control to start measurement from bone density measurement by the second bone density measuring unit without performing bone density measurement (S202 to S205) by the first bone density measuring unit. In contrast to this, if the current examination is the first examination, the control unit 205 proceeds with the process to step S202 to perform bone density measurement (S202 to S205: first bone density measurement) by the first bone density measuring unit. The second bone density measuring unit can perform bone density measurement with the second exposure field based on the bone density measurement result obtained by the first bone density measuring unit. The second bone density measuring unit performs bone density measurement with the second exposure field based on the bone density measurement value obtained by the first bone density measuring unit and a predetermined threshold. The second bone density measuring unit can discriminate whether bone density measurement with the first exposure field is omitted and perform bone density measurement with the second exposure field in accordance with the discrimination result.

(S202: First Imaging)

In the first imaging in step S202, the exposure field setting unit 114 sets the first exposure field to the radiation exposure field aperture 1001 which enables imaging of a plurality of regions (for example, L1 to L4 of the lumbar vertebrae and a hip joint 401 of the femur proximal portion) of the object 103. The control unit 105 performs imaging with the set first exposure field by controlling the radiation imaging apparatus. The control unit 105 makes the radiation generator 104 generate radiation by supplying a high-voltage pulse (pulse signal) to the radiation source 101 upon pressing of the exposure switch. The radiation generator 104 makes the radiation source 101 generate cone-beam radiation by supplying a pulse signal based on a tube voltage to the radiation source 101. The radiation source 101 irradiates the object 103 with cone-beam radiation based on a pulse signal from the radiation generator 104. The radiation source 101 irradiates the object 103 with X-rays with a high voltage V1 (the first tube voltage, for example, 140 kV) once and with a low voltage V2 (the second tube voltage, for example, 80 kV) once. Note that 140 kV as an example of the high voltage V1 and 80 kV as an example of the low voltage V2 are merely exemplary numerical values. The present invention is not limited to these examples, and voltages other than the examples may be used. For example, voltages can be arbitrarily set in accordance with a measurement target region, an image that the user tries to see, the physique of the object 103, or the like.

An additional filter (not shown) is preferably attached to the radiation exposure field aperture 1001 at the time of irradiation with X-rays from the radiation source 101. As the additional filter, for example, a copper plate with a thickness of 0.5 mm can be attached to the radiation exposure field aperture 1001. If an X-ray spectrum includes a low-energy component, radiation quality hardening tends to occur in the body of the object 103. This can also be a factor causing a decrease in bone density calculation accuracy. However, attaching the additional filter will cut the low-energy side of the X-ray spectrum, thereby improving the energy resolution between high-voltage X-rays and low-voltage X-rays.

Figure 3:
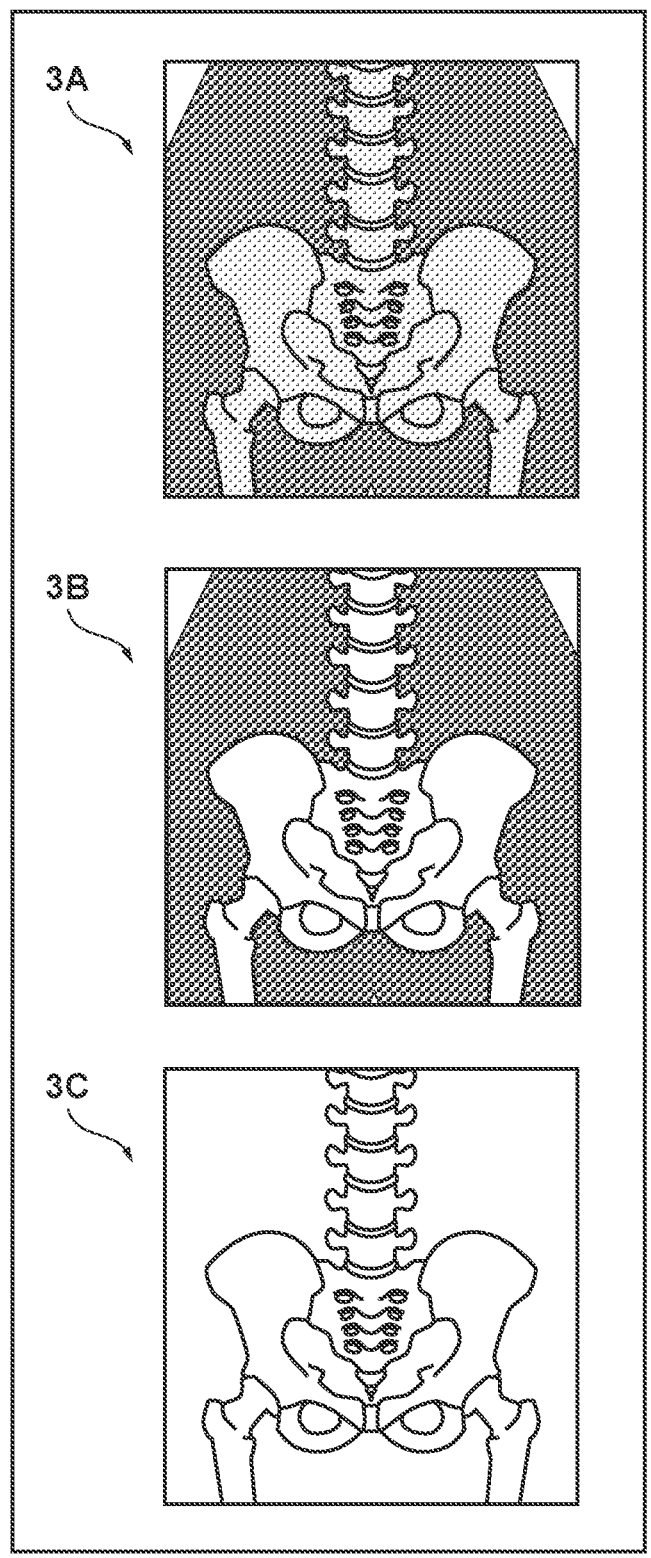
FIG. 3 is a conceptual view showing a high-energy image, a low-energy image, and a bone image.

The FPD 102 creates the high-energy image indicated by 3A of FIG. 3 by high-voltage imaging based on the high voltage V1 and creates low-energy image indicated by 3B of FIG. 3 by low-voltage imaging based on the low voltage V2.

In the first measurement, the radiation exposure field aperture 1001 sets the first exposure field securing a sufficiently wide exposure field (imaging range) in order to simultaneously image the lumbar vertebrae and the femur proximal portion as indicated by 3A and 3B of FIG. 3. This makes it possible to simultaneously measure the bone density of the lumbar vertebra and the femur proximal portion, which are clinically important, by one-time measurement. This can improve the examination throughput and reduce the load on the object 103.

As described above, using the FPD 102 in which radiation detection units (not shown) are stacked can obtain a low-energy image like that indicated by 3B of FIG. 3 from the radiation detection unit on the upper layer and a high-energy image like that indicated by 3A of FIG. 3 from the radiation detection unit on the lower layer by one-time irradiation with X-rays. When the radiation source 101 emits X-rays with the high voltage V1 (for example, 140 kV), since the margin for radiation quality hardening by the radiation detection unit on the upper layer decreases to lead to a decrease in energy resolution, the above additional filter need not be attached. The image obtained by imaging by irradiation with X-rays based on the high voltage V1 is called the high-energy image, and the image obtained by imaging by irradiation with X-rays based on the low voltage V2 is called the low-energy image.

(S203: Creation of Bone Image)

In step S203, the difference image creating unit 110 creates a bone image 303 indicated by 3C of FIG. 3 by calculating the logarithmic difference between the high-energy image indicated by 3A of FIG. 3 and the low-energy image indicated by 3B of FIG. 3, which are obtained by imaging in step S202. The processing performed by the difference image creating unit 110 will be described in detail below. First of all, the high-energy image and the low-energy image can be represented by equations (1) and (2) given below.

$$-ln I_H = -ln I_{H0} + \mu_{HA}\sigma_A + \mu_{HB}\sigma_B \quad (1)$$

$$-ln I_L = -ln I_{L0} + \mu_{LA}\sigma_A + \mu_{LB}\sigma_B \quad (2)$$

In this case, $I_H$ represents the high-energy image indicated by 3A of FIG. 3, and $I_L$ represents the low-energy image indicated by 3B of FIG. 3. The high-energy image and the low-energy image obtained by imaging indicate two-dimensional distributions of pixel values.

In addition, $I_{H0}$ and $I_{L0}$ respectively represent a high-energy image and a low-energy image in the absence of the object 103. In this case, the suffix "H" represents high energy, and the suffix "L" represents low energy. The suffix "A" represents the soft tissue, and the suffix "B" represents the bone (bone region). In addition, $\mu_{HA}$ and $\mu_{LA}$ respectively represent the mass attenuation coefficients of the soft tissues with high energy and low energy, $\mu_{HB}$ and $\mu_{LB}$ respectively represent the mass attenuation coefficients of the bones with high energy and low energy, $\sigma_A$ represents the area density of the soft tissue, and $\sigma_B$ represents a bone area density. The unit of mass attenuation coefficient is $cm^2/g$, and the unit of area density is $g/cm^2$.

In this case, the difference image creating unit 110 creates the bone image (3C of FIG. 3) indicated by equation (3) given below by multiplying equation (1) by $\mu_{LA}/\mu_{HA}$ and subtracting the product from equation (2).

$$\frac{\mu_{LA}}{\mu_{HA}}\ln I_H - \ln I_L = \frac{\mu_{LA}}{\mu_{HA}}\ln I_{H0} - \ln I_{L0} + \left(\mu_{LB} - \frac{\mu_{LA}}{\mu_{HA}}\mu_{HB}\right)\sigma_B \quad (3)$$

(S204: Bone Region Extraction)

In step S204, the bone region extraction unit 111 extracts a bone region (ROI) subjected to bone density calculation from the bone image indicating the distribution of bone portions in the object 103. According to a simplest bone region extraction method, for example, the user can be made to select a bone region on a user interface. However, it is cumbersome and time consuming for the user to extract a bone region by using a mouse or the like. In addition, the repeatability of bone density calculation accuracy decreases when different users extract different bone regions even for the same object or the bone region extracted by even the same user varies every time.

Accordingly, it is preferable to automatically extract a bone region by using segmentation based on image processing. The bone region extraction unit 111 can extract a bone region subjected to bone density calculation from a bone image indicating the distribution of bone portions in the object 103 by using a watershed method, a graph cut method, a grabcut method, or the like as a known segmentation technique. In addition, the bone region extraction unit 111 can extract a bone region from a bone image by using a machine learning technique such as Unet or PSPnet as a bone region extraction method instead of the above segmentation technique.

Figure 4:
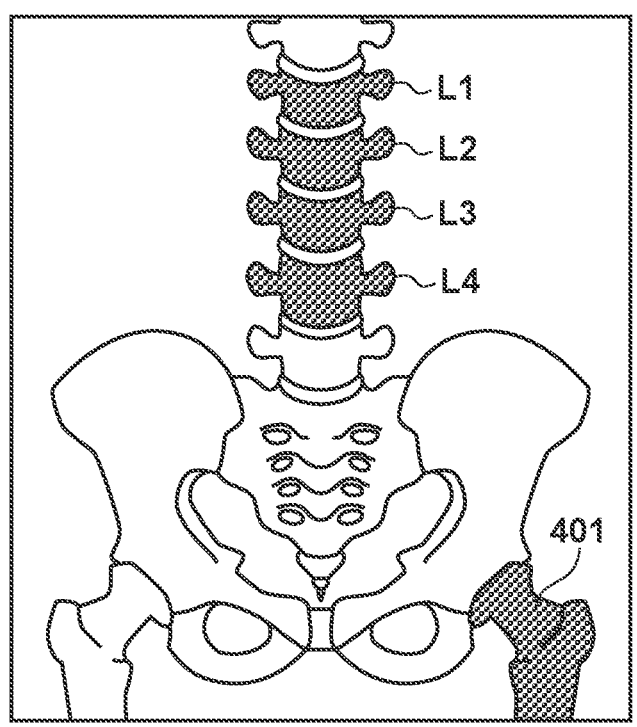
FIG. 4 is a view for explaining the extraction of a bone region.

The bone region extraction unit 111 sets a bone region (analysis region) subjected to bone density calculation from a bone image. FIG. 4 is a view showing an example of the extraction of a bone region. In the example of the extraction of the bone region in FIG. 4, L1 to L4 are extracted as a lumbar vertebra analysis regions, and the hip joint 401 is extracted as an analysis region of the femur proximal portion.

(S205: Bone Density Calculation)

In step S205, the bone density calculation unit 112 calculates the bone density of the bone region (ROI: FIG. 4) extracted by the bone region extraction unit 111 in step S204. The bone density calculation unit 112 sets a soft tissue region near the bone region and corrects the pixel value of the bone region based on the pixel value of the soft tissue region. The bone density calculation unit 112 then calculates the bone density of the bone region based on the corrected pixel value of the bone region.

In calculating a bone density, the bone density calculation unit 112 sets soft tissue regions near bone regions subjected to bone density calculation (for example, regions corresponding to L1 to L4 in FIG. 4 in the case of the lumbar vertebrae). The soft tissue regions will also be referred to as baseline regions hereinafter. As indicated by 5A of FIG. 5, the bone density calculation unit 112 sets baseline regions 501 and baseline regions 502 at positions near the bone regions subjected to bone density calculation so as to include only soft tissues without including any bone regions. The pixel value of the high-energy images (3A of FIG. 3) and the pixel value of the low-energy images (3B of FIG. 3) in the baseline regions 501 and 502 can be respectively expressed by equations (4) and (5) given below. Since the baseline regions 501 and 502 are set so as not include any bone regions, equations (4) and (5) can be represented by the high-energy images ($I_{HA}$, $I_{H0}$), the low-energy images ($I_{LA}$, $I_{L0}$), the mass attenuation coefficients ($\mu_{HA}$, $\mu_{LA}$), and the surface density ($\sigma_A$) in the soft tissue (suffix "A").

$$-\ln I_{HA} = -\ln I_{H0} + \mu_{HA}\sigma_A \quad (4)$$

$$-\ln I_{LA} = -\ln I_{L0} + \mu_{LA}\mu_A \quad (5)$$

In this case, the bone density calculation unit 112 obtains equation (6) given below concerning the difference between the high-energy images and the low-energy images in the baseline regions 501 and 502 (soft tissues) by multiplying equation (4) by $\mu_{LA}/\mu_{HA}$ and subtracting the product from equation (5).

$$\frac{\mu_{LA}}{\mu_{HA}}\ln I_{HA} - \ln I_{LA} = \frac{\mu_{LA}}{\mu_{HA}}\ln I_{H0} - \ln I_{L0} \quad (6)$$

In addition, the bone density calculation unit 112 obtains equation (7) given below by subtracting equation (3) from equation (6).

$$\frac{\mu_{LA}}{\mu_{HA}}(\ln I_H - \ln I_{HA}) - (\ln I_L - \ln I_{LA}) = \left(\mu_{LB} - \frac{\mu_{LA}}{\mu_{HA}}\mu_{HB}\right)\sigma_B \quad (7)$$

The high-energy image $I_{H0}$ and the low-energy image $I_{L0}$ in the absence of the object 103 which are unknown quantities in equation (7) are removed. The left side of equation (7) is proportional to the bone density $\sigma_B$ as indicated by the right side. Equation (7) will be referred to as a bone image after baseline correction.

Figure 5:
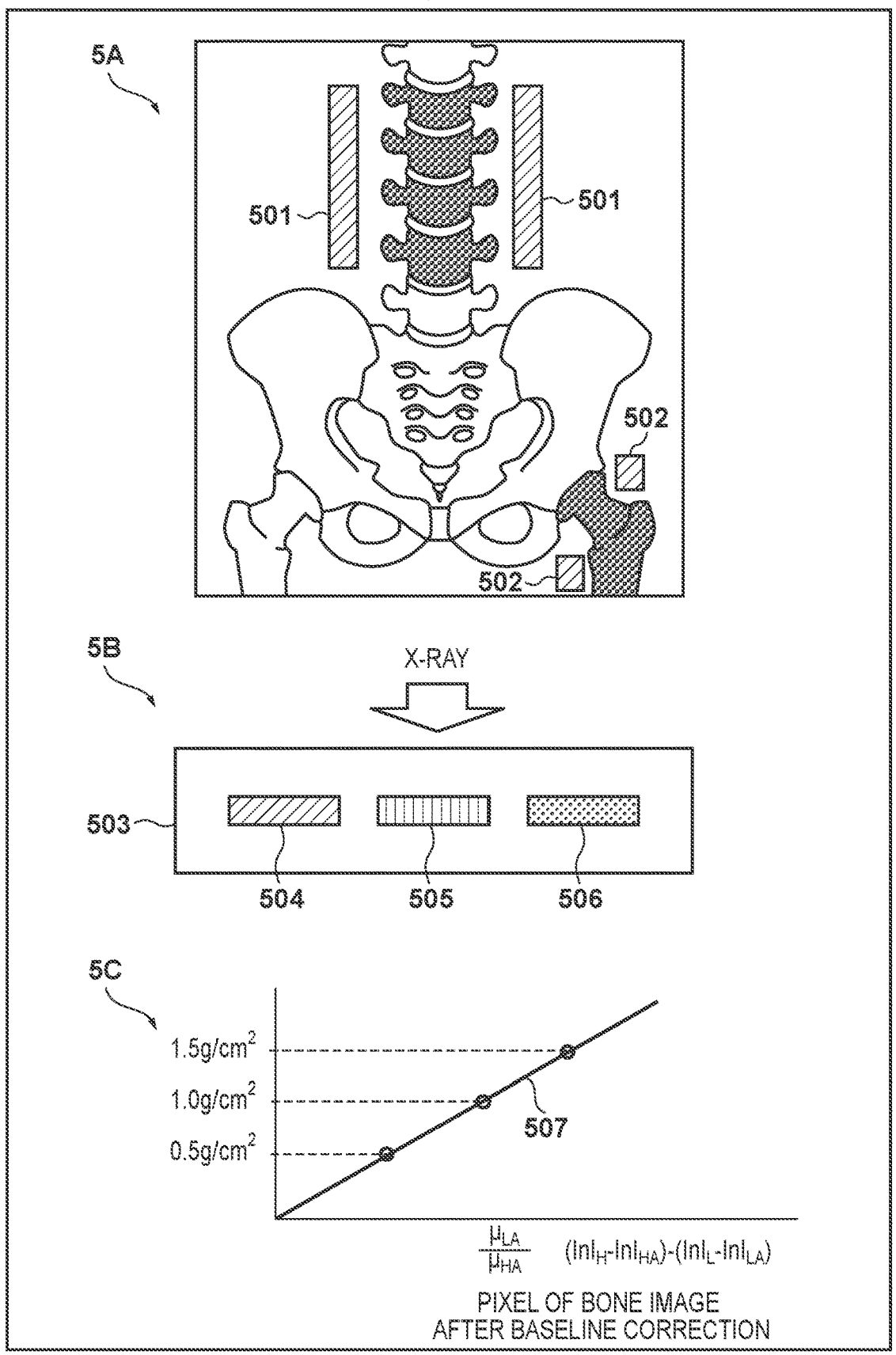
FIG. 5 is a view for explaining the calculation of a baseline region and a calibration curve.

The bone density calculation unit 112 calculates a calibration curve 507 indicated by 5C of FIG. 5 from a calibration phantom 503 indicated by 5B of FIG. 5 and converts the bone image after baseline correction into a bone density $g/cm^2$ by using the calibration curve 507. Specifically, this operation is performed as follows.

The calibration phantom 503 includes a first calibration portion 504, a second calibration portion 505, and a third calibration portion 506. The first calibration portion 504, the second calibration portion 505, and the third calibration portion 506 of the calibration phantom 503 respectively have bone densities of 0.5 $g/cm^2$, 1.0 $g/cm^2$, and 1.5 $g/cm^2$. The calibration phantom 503 indicated by 5B of FIG. 5 is imaged under the same conditions as those for the object 103 to create a bone image after baseline correction which is represented by equation (7). This makes it possible to obtain the calibration curve 507 like that indicated by 5C of FIG. 5. The calibration curve 507 indicated by 5C of FIG. 5 represents the relationship between the bone density (ordinate) and the pixel value (abscissa) of the bone image after baseline correction.

Finally, the bone density calculation unit 112 converts the pixel value of the bone image after baseline correction created based on imaging of the object 103 into the bone density $g/cm^2$ by using the calibration curve 507. Note that the calibration phantom 503 indicated by 5B of FIG. 5 is preferably imaged and the calibration curve 507 is preferably obtained before one-day examination.

(S206: Determination of Osteoporosis Suspicion)

In step S206, the bone density determination unit 113 performs osteoporosis determination based on the average bone density of L1 to L4 of the lumbar vertebrae in FIG. 4 and the bone density of the hip joint 401 of the femur proximal portion which are calculated in step S205. For example, the bone density determination unit 113 performs osteoporosis diagnosis by comparison with the YAM value according to a primary osteoporosis diagnosis criterion. In this case, the YAM value is the average value of bone densities of young adults (20 to 44 years old). According to the primary osteoporosis diagnosis criterion, if the bone density of the object is 70% to 80% of the YAM value, a reduction in bone mass is diagnosed, whereas if the bone density is 70% or less than the YAM value, primary osteoporosis is diagnosed. The bone density determination unit 113 determines osteoporosis by comparing the YAM value with the average bone density of L1 to L4 of the lumbar vertebrae and the bone density of the hip joint 401 of the femur proximal portion based on the primary osteoporosis diagnosis criterion.

If the bone density determination unit 113 determines in step S206 that the bone density of each region of the object 103 is less than 80% of the YAM value (S206: YES), the control unit 105 proceeds with the process to step S207 (exposure field change) and shifts to preparation for second imaging in step S208. The control unit 105 controls bone density measurement by the first bone density measuring unit (S202 to S205) and bone density measurement by the second bone density measuring unit (S208 to S210). If the bone density measurement value obtained by the first bone density measuring unit is lower than a predetermined value, the control unit 105 shifts the process to perform bone density measurement by the second bone density measuring unit. If the bone density measurement value of each of a plurality of regions obtained by the first bone density measuring unit is lower than the predetermined value, the control unit 105 performs bone density measurement with respect to each region by using the second bone density measuring unit.

If the bone density determination unit 113 determines in step S206 that the bone density of each region of the object 103 is equal to or more than the YAM value (S206: NO), the control unit 105 determines based on the determination result (discrimination result) that the possibility of osteoporosis is low and terminates the examination.

(S207: Exposure Field Change)

In step S206 described above, the exposure field setting unit 114 sets the second exposure field for measurement by the second bone density measuring unit based on the bone density measurement result obtained by the first bone density measuring unit (S206: YES). That is, if the bone density determination unit 113 determines that there is suspicion of osteoporosis, the exposure field setting unit 114 changes the exposure field by narrowing down the radiation exposure field aperture 1001. In the measurement (S202 to S205) by the first bone density measuring unit, the exposure field setting unit 114 sets the first exposure field that enables imaging of a plurality of regions of the object. In the measurement (S208 to S210) by the second bone density measuring unit, the exposure field setting unit 114 sets the second exposure field that enables imaging of at least some of a plurality of regions. In this case, the first exposure field includes the lumbar vertebrae and the femur proximal portion as a plurality of regions of the object 103, and the second exposure field includes either the lumbar vertebrae or the femur proximal portion as some of a plurality of regions. Since regions other than the second exposure field are not irradiated with radiation, it is possible to suppress an increase in the dosage on the object 103.

In the first imaging in step S202, the exposure field setting unit 114 sets the first exposure field that enables imaging of a plurality of regions of the object 103 (for example, L1 to L4 of the lumbar vertebrae and the hip joint 401 of the femur proximal portion) in the radiation exposure field aperture 1001. In contrast to this, in step S202, the exposure field setting unit 114 sets the second exposure field that is narrower than the first exposure field and enables imaging of at least some of a plurality of regions in the radiation exposure field aperture 1001.

The exposure field setting unit 114 can set the second exposure field by using a learned model associated with the setting of an exposure field corresponding to a region subjected to measurement by the second bone density measuring unit.

Figure 6:
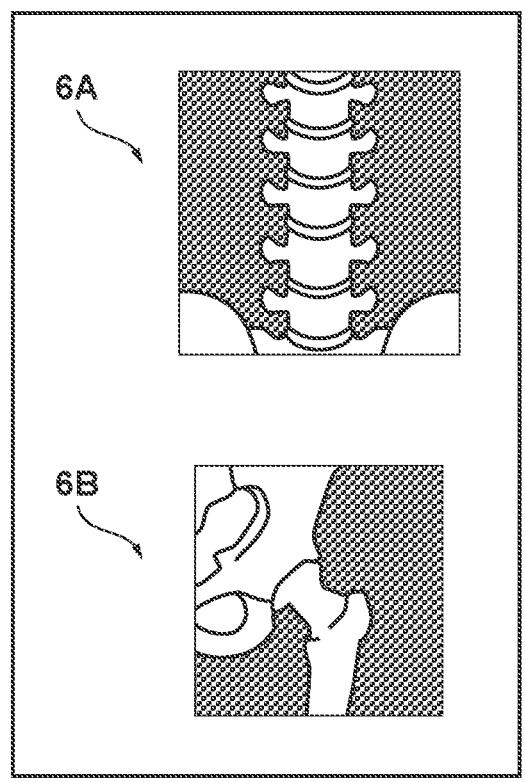
FIG. 6 is a view for explaining an example of the setting of an exposure field range according to the first embodiment.

If the bone density determination unit 113 determines in step S206 described above that the average value of the bone densities of L1 to L4 of the lumbar vertebrae indicates a bone density reduction, the exposure field setting unit 114 narrows down the exposure field in this step so as to include L1 to L4 of the lumbar vertebrae as at least some of a plurality of regions (L1 to L4 of the lumbar vertebrae and the hip joint 401 of the femur proximal portion) as indicated by 6A of FIG. 6. That is, the exposure field setting unit 114 changes the setting of the radiation exposure field aperture 1001 so as to narrow down the exposure field to the second exposure field narrower than the first exposure field.

If the bone density determination unit 113 determines in step S206 that a bone density reduction has occurred in the hip joint 401 of the femur proximal portion, the exposure field is narrowed down to include only the hip joint 401 as indicated by 6B of FIG. 6. In step S206, the exposure field setting unit 114 narrows down the exposure field so as to include the hip joint 401 as at least some of a plurality of regions (L1 to L4 of the lumbar vertebrae and the hip joint 401 of the femur proximal portion) as indicated by 6B of FIG. 6. That is, as in the case of the lumbar vertebrae, the exposure field setting unit 114 changes the setting of the radiation exposure field aperture 1001 so as to narrow down the exposure field to the second exposure field narrower than the first exposure field.

If the radiation exposure field aperture 1001 can be electrically controlled in synchronism with the radiation imaging system 100, it is possible to automatically narrow down the exposure field by using the bone region extraction result in step S204. Alternatively, when the exposure field setting is changed manually, the control unit 105 can also perform display control so as to display, on the monitor 106, an instruction to narrow down the exposure field in accordance with the region with respect to the user.

(S208: Second Imaging)

In step S208, the control unit 105 controls the radiation imaging apparatus to generate radiation by supplying a pulse signal to the radiation source 101 from the radiation generator 104 upon pressing of the exposure switch. In the second imaging in step S208, imaging is performed with the second exposure field set and changed in step S207. The second exposure field is narrower than the first exposure field used in the first imaging (S202), and the exposure field is narrowed down to image at least some of a plurality of regions. The second imaging processing is the same as the first imaging in step S202 except that the exposure field is narrowed and one region is set as an imaging target region as indicated by 6A and 6B of FIG. 6, and hence a detailed description of the imaging will be omitted.

(S209: Bone Image Creation)

In step S209, the difference image creating unit 110 creates a bone image by calculating the logarithmic difference between the high-energy image and the low-energy image obtained by imaging in step S208. The image difference processing in step S209 is the same as that in step S203 except that the exposure field is narrowed down and one region is set as an imaging target region as indicated by 6A and 6B of FIG. 6, and hence a detailed description of the image difference processing will be omitted.

(S210: Bone Region Extraction)

In step S210, the bone region extraction unit 111 extracts a bone region (ROI) subjected to bone density calculation from a bone image. The bone region extraction processing in this step is the same as that in step S204. Accordingly, the bone region extraction unit 111 can use the result obtained in step S204 without any change and without extracting any bone region. That is, the bone region extraction unit 111 can apply the extraction result of the bone region extracted by the first bone density measuring unit to the extraction of a bone region in the measurement performed by the second bone density measuring unit. Using the same bone region as that extracted in step S204 makes it possible to more accurately grasp the difference (change) between the first bone density measurement in the first imaging and the second bone density measurement in the second imaging.

On the other hand, in some case, the body of the object 103 has moved between the first bone density measurement and the second bone density measurement. In this case, a bone region may be extracted again.

According to this embodiment, in screening examination such as initial visit examination or check-up examination, first of all, first bone density measurement based on first imaging is performed to simultaneously measure the bone densities of a plurality of regions (for example, the lumbar vertebrae and the femur proximal portion) of the object. If it is determined in the first bone density measurement that there is a suspicion of osteoporosis, the exposure field is narrowed down to a specific region in the second bone density measurement based on the second imaging to perform precise bone density measurement with reduced scattered rays. This can shorten the examination time in measurement of the bone densities of many objects such as screening examination and reduce the load on the objects and the user by improving the throughput.

Second Embodiment

The first embodiment has exemplified the case in which the first bone density measuring unit and the second bone density measuring unit perform imaging with two tube voltages (V1 and V2). The second embodiment will exemplify an arrangement in which the first bone density measuring unit performs bone density measurement based on the image data obtained by an FPD 102 (image obtaining unit) in accordance with the radiation generated with a single tube voltage. Note that the arrangement of a radiation imaging system 100 (FIG. 1) is the same as that in the first embodiment.

Figure 7:
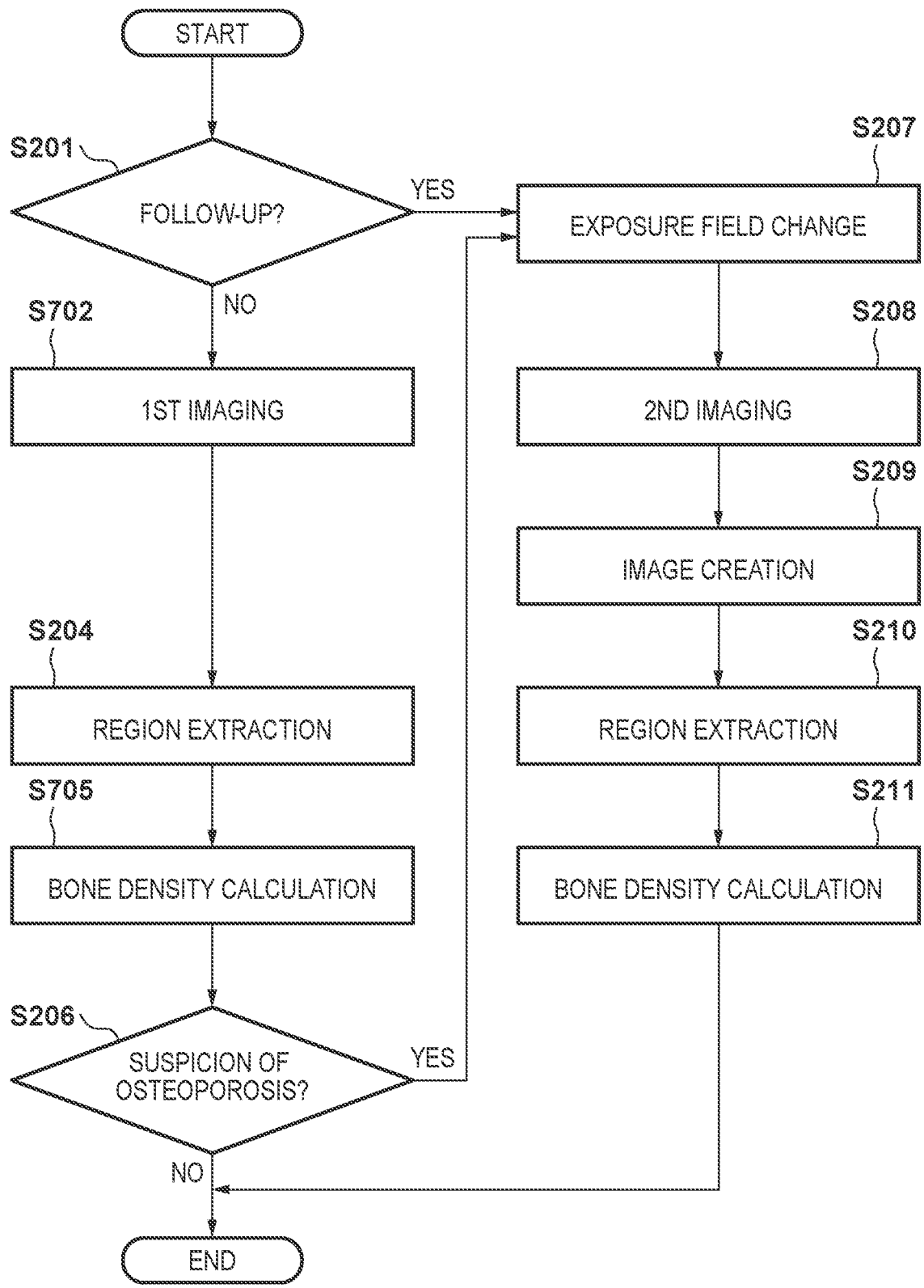
FIG. 7 is a flowchart for explaining a processing procedure in an image processing unit according to the second embodiment.

Processing in an image processing unit 109 according to the second embodiment will be described with reference to the flowchart shown in FIG. 7. This processing differs from the processing (FIG. 2) performed by the image processing unit 109 according to the first embodiment in processing in steps S702 and S705, and hence only different portions in the processing will be described.

(S702: First Measurement)

In the first imaging in step S702, a control unit 105 performs imaging with the first exposure field set by controlling a radiation imaging apparatus. The control unit 105 causes a radiation source 101 to generate radiation by supplying a high-voltage pulse (pulse signal) to the radiation source 101 from a radiation generator 104 upon pressing of the exposure switch. The radiation source 101 irradiates an object 103 with X-rays based on a pulse signal from the radiation generator 104. The radiation source 101 irradiates the object 103 with X-rays based on a single tube voltage (for example, 140 kV). The tube voltage (for example, 140 kV) corresponds to the high voltage V1 described in the first embodiment. The FPD 102 obtains a high-energy image based on the tube voltage (high voltage V1). In addition, bone density measurement is approximately performed by using the technique described in step S705 below.

Accordingly, in the first bone density measurement based on the first imaging, imaging is performed with the single tube voltage (high voltage V1), and hence control on the radiation generator 104 is facilitated. This makes it possible to, for example, perform bone density measurement while performing fluoroscopic imaging for positioning.

(S705: Bone Density Calculation)

In the first measurement (S702) according to the second embodiment, since imaging is performed with the single tube voltage, a bone density calculation unit 112 calculates the bone density of a bone region (ROI: FIG. 4) extracted in step S204 by a bone region extraction unit 111 by using the following approximate method.

As described in the first embodiment, the pixel value of the bone region (FIG. 4) in the high-energy image can be represented by equation (8) given below.

$$-lnI_H = -lnI_{H0} + \mu_{HA}\sigma_A + \mu_{HB}\sigma_B \quad (8)$$

The pixel values of baseline regions 501 and 502 (5A of FIG. 5) formed from soft tissues can be represented by equation (9) given below.

$$-lnI_{HA} = -lnI_{H0} + \mu_{HA}\sigma_A^b \quad (9)$$

In this case, an area density σ is obtained by multiplying a volume density ρ by a thickness d of the tissue. Accordingly, if the baseline regions and the bone region can be approximately regarded to have the same thickness, approximation by equation (10) given below holds.

$$\sigma_A^b = \rho_A d_A^b \cong \rho_A(d_A + d_B) = \sigma_A + \rho_A d_B \quad (10)$$

In this case, the superscript "b" represents the baseline region, the subscript "A" represents the soft tissue, and the subscript "B" represents the bone. Approximation by equation (10) holds when a baseline region is near a bone region in the human body.

Accordingly, the bone density calculation unit 112 can obtain formula (11) by substituting equation (10) into equation (9), subtracting the result from equation (8), and rearranging the result.

$$-\ln I_H + \ln I_{HA} \cong \left(\mu_{HB} - \frac{\mu_{HA}\rho_A}{\rho_B}\right)\sigma_B \quad (11)$$

A high-energy image $I_{H0}$ in the absence of the object 103 which is an unknown quantity in equation (8) is removed, and a bone image after approximate baseline correction can be obtained. Conversion to an actual bone density g/cm² is the same as in the first embodiment, and the bone density calculation unit 112 converts the pixel value of the bone image after baseline correction into the bone density g/cm² by using a calibration phantom 503 indicated by 5B of FIG. 5 and a calibration curve 507 indicated by 5C of FIG. 5.

According to this embodiment, approximate bone density measurement can be performed by performing the first bone density measurement with the single tube voltage. For a region determined by the first bone density measurement to have suspicion of osteoporosis, precise bone density measurement is performed with two or more tube voltages by the second bone density measurement by the processing in steps S207 to S211. This makes it possible to seamlessly shift to the precise second bone density measurement by positioning while observing the bone density using a moving image with a diagnosis device capable of moving-image imaging, such as an X-ray TV.

Note that in bone density measurement by the second bone density measuring unit (S207 to S211), the second bone density measuring unit performs bone density measurement based on the image data obtained by the FPD 102 (image obtaining unit) in accordance with the radiation emitted with a plurality of tube voltages including a single tube voltage. That is, the second bone density measuring unit performs bone density measurement by using the image data obtained by bone density measurement by the first bone density measuring unit and the image data obtained by the FPD 102 (image obtaining unit) with a tube voltage different from the single tube voltage. Using the image data obtained by bone density measurement by the first bone density measuring unit for bone density measurement by the second bone density measuring unit can suppress an increase in the dosage on the object 103 and accurately perform bone density measurement by performing measurement using image data with a plurality of tube voltages.

Third Embodiment

The first embodiment has exemplified the arrangement in which the first bone density measurement based on the first imaging is performed to simultaneously measure the bone densities of a plurality of regions of the object 103, and when it is determined in the first bone density measurement that there is suspicion of osteoporosis, the exposure field is narrowed down to a specific region in the second bone density measurement based on the second imaging to perform precise bone density measurement with reduced scattered rays. The third embodiment will exemplify an arrangement in which when the second bone density measuring unit performs the second bone density measurement based on the second imaging, an exposure field setting unit 114 sets a plurality of exposure fields. Note that the arrangement (FIG. 1) of a radiation imaging system 100 is the same as that in the first embodiment.

Figure 8:
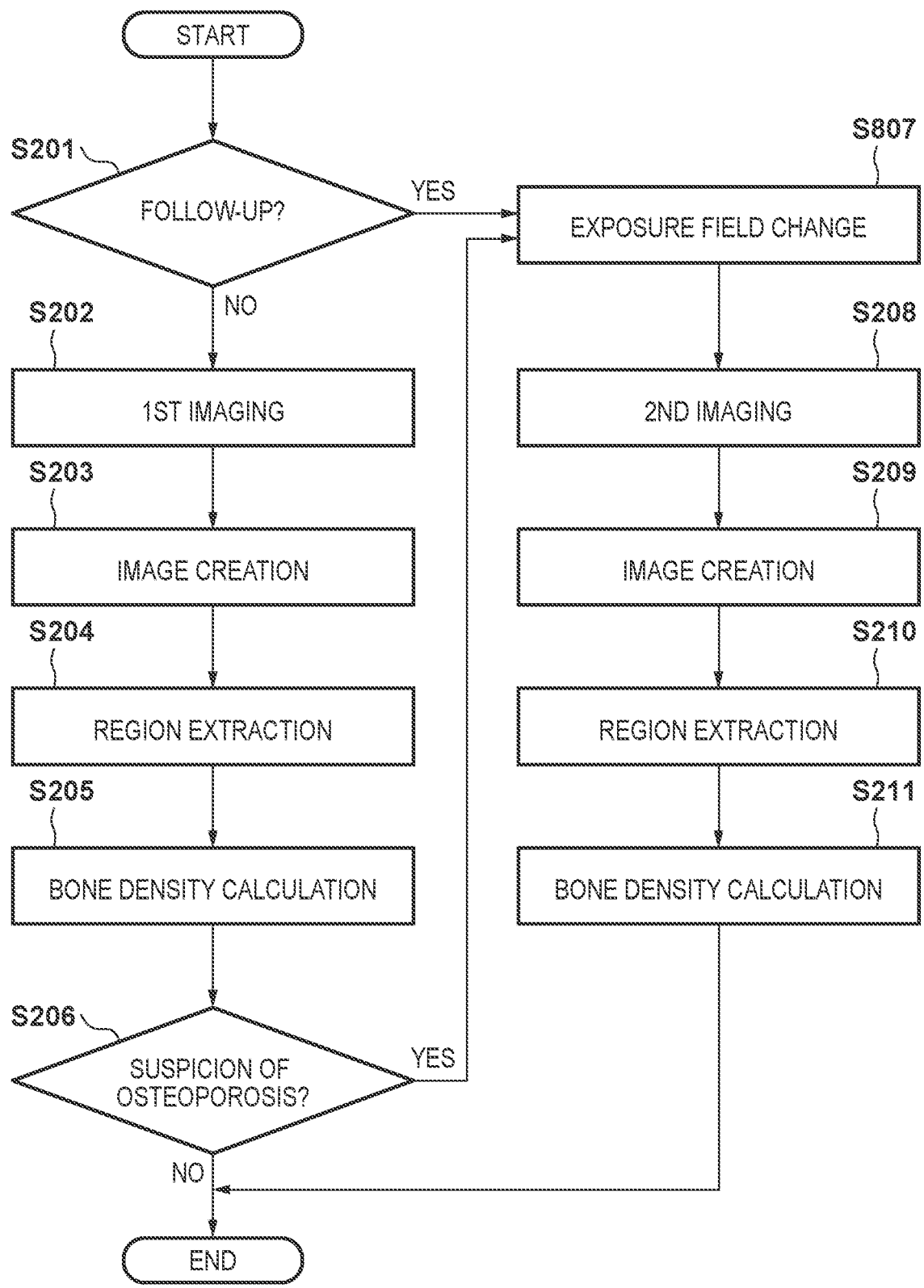
FIG. 8 is a flowchart for explaining a processing procedure in an image processing unit according to the third embodiment.

Processing in an image processing unit 109 according to the third embodiment will be described with reference to the flowchart shown in FIG. 8. This processing differs from the processing (FIG. 2) performed by the image processing unit 109 according to the first embodiment in processing in step S807, and hence only different portions in the processing will be described.

If a bone density determination unit 113 determines in step S206 in the first bone density measurement that there is suspicion of osteoporosis (S206: YES), the exposure field setting unit 114 changes the exposure field by narrowing down a radiation exposure field aperture 1001 (S207). The exposure field setting unit 114 sets a plurality of exposure fields. The bone density measuring unit according to this embodiment performs bone density measurement based on the image data obtained by an FPD 102 (image obtaining unit) with a plurality of exposure fields set by the exposure field setting unit 114.

The plurality of exposure fields include each region of the object subjected to bone density measurement, and regions other than the plurality of exposure fields are not irradiated with radiation.

Figure 9:
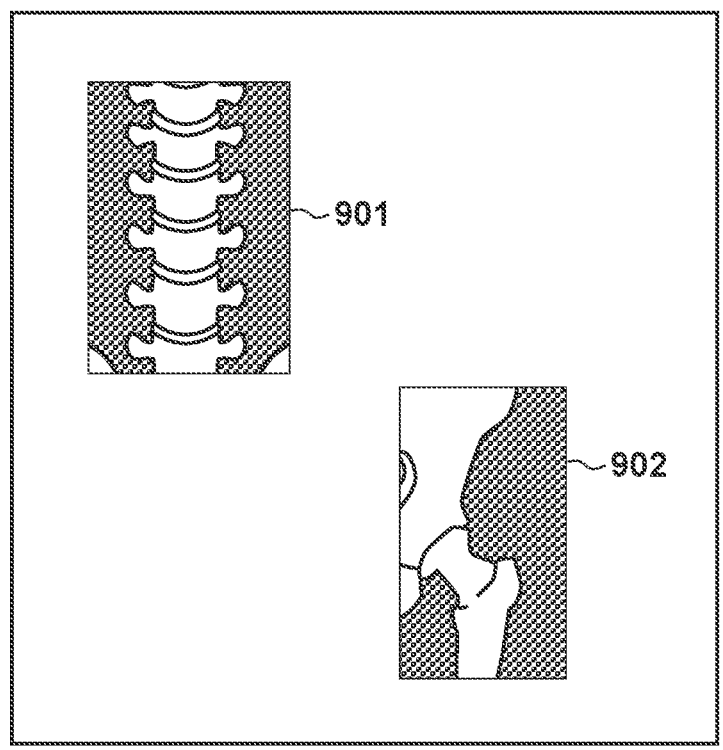
FIG. 9 is a view for explaining an example of the setting of an exposure field range according to the third embodiment.

In this case, the first exposure field set in the first imaging (S202) is the single exposure field in which an imaging range is secured to allow simultaneous imaging of a plurality of regions. In this step, the exposure field setting unit 114 changes the setting of the radiation exposure field aperture 1001 so as to separate the single first exposure field into a plurality of exposure fields respectively corresponding to the positions of a plurality of regions (for example, L1 to L4 of the lumbar vertebrae and a hip joint 401 of the femur proximal portion) of an object 103. FIG. 9 is a view for explaining a setting example of the exposure field in the third embodiment. As shown in FIG. 9, the exposure field setting unit 114 separates the first exposure field (single exposure field) into an exposure field 901 corresponding to the lumbar vertebrae (L1 to L4) and an exposure field 902 corresponding to the hip joint 401 of the femur proximal portion by changing the setting of the radiation exposure field aperture 1001.

In step S208, imaging is performed with the second exposure field set and changed in step S207. A control unit 105 controls the radiation imaging apparatus to cause a radiation source 101 to generate radiation by supplying a pulse signal to the radiation source 101 from a radiation generator 104 upon pressing of the exposure switch, thereby simultaneously imaging the lumbar vertebrae (L1 to L4) and the hip joint 401 of the femur proximal portion.

In step S211, a bone density calculation unit 112 simultaneously calculates the bone densities of a plurality of bone regions (ROIs: FIG. 4) extracted by a bone region extraction unit 111 in step S210.

According to this embodiment, setting a plurality of exposure fields in the second bone density measurement based on the second imaging makes it possible to perform accurate bone density measurement with reduced scattered rays while simultaneously measuring the bone densities of a plurality of regions. For example, the plurality of regions include the lumbar vertebrae that allow easy determination of the medicinal effects of medicines and the femur proximal portion as a region that tends to make the object bedridden when broken. That is, these regions are clinically important, and hence the embodiment is effective when accurate bone density measurement with reduced scattered rays is performed while the both regions are simultaneously measured.

The present invention can provide a radiation imaging technique that can improve the examination efficiency and the measurement accuracy while reducing the dosage on an object.

Other Embodiments

Embodiment(s) of the present invention can also be realized by a computer of a system or apparatus that reads out and executes computer executable instructions (e.g., one or more programs) recorded on a storage medium (which may also be referred to more fully as 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
an image obtaining unit configured to obtain image data corresponding to incident radiation; and
an image processing unit configured to perform first bone density measurement based on image data obtained by the image obtaining unit with a first exposure field, and perform second bone density measurement based on image data obtained by the image obtaining unit with a second exposure field that is narrower then the first exposure field.

2. The radiation imaging apparatus according to claim 1, further comprising an exposure field setting unit configured to set an exposure field of the radiation, wherein
the exposure field setting unit sets the first exposure field that enables imaging of a plurality of regions of an object in the first bone density measurement, and sets the second exposure field that enables imaging of at least some of the plurality of regions in the second bone density measurement with an exposure field that is narrower than the first exposure field.

3. The radiation imaging apparatus according to claim 2, wherein the first exposure field includes a lumbar vertebra and a femur proximal portion as the plurality of regions, and the second exposure field includes one of lumbar vertebra and the femur proximal portion as the some of the regions.

4. The radiation imaging apparatus according to claim 2, wherein the exposure field setting unit sets the second exposure field by using a learned model associated with setting of an exposure field corresponding to a region subjected to the second bone density measurement.

5. The radiation imaging apparatus according to claim 2, wherein the exposure field setting unit sets the second exposure field based on a result obtained by the first bone density measurement.

6. The radiation imaging apparatus according to claim 2, wherein the radiation is not applied to a region other than the second exposure field.

7. The radiation imaging apparatus according to claim 1, further comprising a control unit configured to control the image processing unit so as to execute the first bone density measurement and the second bone density measurement.

8. The radiation imaging apparatus according to claim 7, wherein the control unit shifts a process to perform the second bone density measurement when a measurement value obtained by the first bone density measurement is lower than a predetermined value.

9. An information processing apparatus comprising an image processing unit configured to perform first bone density measurement based on image data obtained in accordance with radiation in a first exposure field and to perform second bone density measurement based on image data obtained in accordance with radiation in a second exposure field that is narrower than the first exposure field.

10. The information processing apparatus according to claim 9, wherein the image processing unit performs the second bone density measurement with the second exposure field based on a result obtained by the first bone density measurement.

11. The information processing apparatus according to claim 9, wherein the image processing unit performs the second bone density measurement with the second exposure field based on a measurement value obtained by the first bone density measurement and a predetermined threshold.

12. The information processing apparatus according to claim 9, wherein the image processing unit discriminates whether to omit the first bone density measurement with the first exposure field and performs the second bone density measurement with the second exposure field in accordance with a discrimination result.

13. The information processing according to claim 9, wherein the image processing unit comprises a creating unit configured to create a bone image indicating a bone distribution based on a difference between image data corresponding to radiation based on a first tube voltage and image data corresponding to radiation based on a second tube voltage, an extraction unit configured to extract a bone region subjected to bone density measurement from the bone image, and a calculation unit configured to calculate a bone density of the bone region, and
the calculation unit sets a soft tissue region near the bone region, corrects a pixel value of the bone region based on a pixel value of the soft tissue region, and calculates a bone density of the bone region based on the corrected pixel value of the bone region.

14. The information processing according to claim 13, wherein the extraction unit applies an extraction result of the bone region extracted in the first bone density measurement to extraction of a bone region in the second bone density measurement.

15. The information processing according to claim 9, wherein in the first bone density measurement, the first bone density measurement is performed based on image data obtained in accordance with radiation generated with a single tube voltage, and in the second bone density measurement, the second bone density measurement is performed based on image data obtained in accordance with radiation generated with a plurality of tube voltages including the signal tube voltage.

16. The information processing according to claim 9, wherein in the second bone density measurement, the second bone density measurement is performed by using the image data obtained in the first bone density measurement and image data obtained in accordance with radiation generated with a tube voltage different from the signal tube voltage.

17. A radiation imaging system, comprising:
a radiation detection apparatus; and
the information processing apparatus according to claim 9, which is configured to process image data obtained from the radiation detection apparatus.

18. The radiation imaging system according to claim 17, further comprising a generating unit configured to generate the radiation, wherein
the generating unit generates cone-beam radiation by supplying a pulse signal based on a tube voltage to a radiation source.

19. The radiation imaging system according to claim 17, further comprising a generating unit configured to generate the radiation, wherein
the generating unit generates the radiation based on a first tube voltage and the radiation based on a second tube voltage lower than the first tube voltage.

20. The radiation imaging system according to claim 17, further comprising a generating unit configured to generate the radiation; and
an exposure field setting unit configured to set an exposure field of the radiation, wherein
a size of a radiation exposure field aperture provided on the generating unit is changed in accordance with a size of the exposure field set by the exposure field setting unit.

21. A radiation imaging method for a radiation imaging apparatus including an image obtaining unit configured to obtain image data corresponding to incident radiation, the method comprising:
a first step of performing first bone density measurement based on image data obtained by the image obtaining unit with a first exposure field; and
a second step of performing second bone density measurement based on image data obtained by the obtaining unit with a second exposure field that is narrower than the first exposure field.

22. A non-transitory computer-readable storage medium storing a program for causing a computer to execute the method according to claim 21.

23. A radiation detection apparatus, comprising:
a pixel array for creating a signal corresponding to radiation, wherein
the radiation detection apparatus obtains image data for performing first bone density measurement in a first exposure field, and
obtains image data for performing second bone density measurement in a second exposure field narrower than the first exposure field.

24. An information processing method comprising an image processing unit configured to perform first bone density measurement based on image data obtained in accordance with radiation in a first exposure field and to perform second bone density measurement based on image data obtained in accordance with radiation in a second exposure field narrower than the first exposure field.

25. A non-transitory computer-readable storage medium storing a program for causing a computer to execute the method according to claim 24.

* * * * *